(12) United States Patent
Gott et al.

(10) Patent No.: US 6,391,835 B1
(45) Date of Patent: May 21, 2002

(54) ALKYL DIOL IMPREGNATE DRY CLEANSING WIPE

(75) Inventors: Robert Edward Gott, Norwalk; Craig Stephen Slavtcheff, Guilford, both of CT (US)

(73) Assignee: Unilever Home & Personal Care USA division of Conopco Inc., Greenwich, CT (US)

( * ) Notice: Subject to any disclaimer, the term of this patent is extended or adjusted under 35 U.S.C. 154(b) by 0 days.

(21) Appl. No.: 09/691,568

(22) Filed: Oct. 18, 2000

Related U.S. Application Data

(60) Provisional application No. 60/197,482, filed on Apr. 17, 2000.

(51) Int. Cl.$^7$ .............................................. C11D 17/00
(52) U.S. Cl. ........................................................ 510/143
(58) Field of Search ..................... 424/402; 510/295, 510/143

(56) References Cited

U.S. PATENT DOCUMENTS

| | | | |
|---|---|---|---|
| 3,975,294 A | | 8/1976 | Dumoulin |
| 5,091,102 A | * | 2/1992 | Sheridan ...................... 252/91 |
| 5,830,487 A | * | 11/1998 | Klofta et al. ............... 424/402 |
| 5,863,663 A | | 1/1999 | Mackey et al. |
| 5,919,471 A | * | 7/1999 | Saferstein et al. .......... 424/402 |
| 5,951,991 A | | 9/1999 | Wagner et al. |
| 5,952,043 A | | 9/1999 | Mackey et al. |
| 5,980,931 A | | 11/1999 | Fowler et al. |
| 5,996,797 A | * | 12/1999 | Flaig .......................... 206/494 |

FOREIGN PATENT DOCUMENTS

| | | |
|---|---|---|
| DE | 199 03 717 | 1/1999 |
| FR | 2 538 238 | 12/1982 |
| WO | 97/34519 | 9/1997 |
| WO | 99/55303 | 11/1999 |
| WO | 99/63962 | 12/1999 |

OTHER PUBLICATIONS

International Search Report.

* cited by examiner

*Primary Examiner*—John Hardee
(74) *Attorney, Agent, or Firm*—Milton L. Honig

(57) ABSTRACT

A disposable substantially dry cleansing article is disclosed having a lathering surfactant and a $C_5-C_{12}$ alkyl diol impregnated into a flexible substrate such as a non-woven cloth. The alkyl diol primarily is a process aid which may concurrently improve aesthetics and increase latherability. Hexylene glycol is the preferred diol. Best performance is achieved with an alkyl diol to total lathering surfactant weight ratio from about 1:1 to about 1:8.

7 Claims, No Drawings

ALKYL DIOL IMPREGNATE DRY CLEANSING WIPE

This appln claims benefit of No. 60/197,482 Apr. 17, 2000.

BACKGROUND OF THE INVENTION

1. Field of the Invention

The invention concerns low-cost, easily manufacturable disposable single use, substantially dry, cleansing articles.

2. The Related Art

Personal cleansing and conditioning products have traditionally been marketed in a variety of forms such as bar soaps, creams, lotions, and gels. These formulations have attempted to satisfy a number of criteria to be acceptable to consumers. These criteria include cleansing effectiveness, skin feel, skin mildness and lather volume. Ideal personal cleansers should gently cleanse the skin or hair, cause little or no irritation, and not leave the skin or hair overly dry after frequent use.

A series of granted and pending patent applications have been published by Procter & Gamble describing substantially dry, disposable, personal cleansing products which address many of the aforementioned functionality concerns. These products are substantially dry articles having deposited onto a woven or non-woven cloth a cleansing composition of surfactant, structurant, skin conditioning agent and other performance ingredients. U.S. Pat. No. 5,951,991 (Wagner et al.) focuses on providing the substrate with a conditioning emulsion separately impregnated from the lathering surfactant onto the cloth substrate. U.S. Pat. No. 5,980,931 (Fowler et al.) emphasizes impregnation of oil soluble conditioning agents. WO 99/55303 (Albacarys et al.) describes skin care actives formulated with the cleansing composition. Manufacturing processes for these products are reported in U.S. Pat. No. 5,952,043 and U.S. Pat. No. 5,863,663, both to Mackey et al. These patents teach use of a continuous lipid phase with a high melting waxy material deposited onto the wipe substrate. The material is intended to be sufficiently brittle so as to be easily disrupted by low shear contact (e.g. during wiping of the skin) to readily release an internal skin conditioning phase, yet the material is required to be sufficiently tough to avoid premature release of the internal phase during the rigors of processing. A problem with this technology is that through compromise the continuous external lipid phase/internal polar phase is neither sufficiently robust for processing and handling nor sufficiently releasable under wash conditions to allow efficient release of conditioning agent onto the skin. A better wipe impregnation and skin conditioning system has been sought.

Accordingly, it is an object of the present invention to provide a disposable, substantially dry cleansing product featuring lathering surfactants deposited with an improved impregnation system onto a wiping article.

Another object of the present invention is to provide a disposable, substantially dry cleansing product having a cleansing composition coating on a flexible wiping cloth wherein the composition adheres without either brittleness or tackiness onto the cloth.

Still another object of the present invention is to provide a disposable, substantially dry cleansing product which includes an impregnation system allowing for improved manufacturability, better aesthetics and increased latherability.

These and other objects of the present invention will become more apparent in light of the following summary and disclosure.

SUMMARY OF THE INVENTION

A substantially dry cleansing product is provided which includes:

(i) a water insoluble substrate;

(ii) a lathering surfactant; and (iii) a $C_5$–$C_{12}$ alkyl diol, the diol and total lathering surfactant being present in a weight ratio from about 1:1 to about 1:8.

Advantageously very small amounts of water may be present in the impregnated composition. Preferably the combined weight of alkyl diol and water to lathering surfactant may be in a weight ratio from about 3:1 to about 1:5.

DETAILED DESCRIPTION OF THE INVENTION

Now it has been discovered that $C_5$–$C_{12}$ alkyl diols can be used to impregnate lathering surfactants onto a wiping article. Improved latherability can be obtained while minimizing the problem of stickiness. Additionally, process advantages are obtained because water used as a traditional carrier for impregnation can be minimized. Phase stability of the coating solution is enhanced by the use of the diol. It has further been found that the improved properties are achieved through control of the weight ratio between the diol and lathering surfactant. Weight ratios of diol to total lathering surfactant should range from about 1:1 to about 1:8, preferably from about 1:2 to about 1:6, optimally from about 1:2.5 to about 1:4.

Advantageously small amounts of water may be present in the impregnated compositions. These amounts should not exceed 20% but may range from about 1 to about 15% by weight. Diols and water relative to total surfactant may be present in a weight ratio from about 3:1 to about 1:5, preferably from about 2:1 to about 1:2, optimally about 1:1. With weight ratios lower than 1:5, the product may be difficult to coat without adding water to reduce viscosity, but thereby forcing a costly drying step. Moreover, these lower ratios are likely to be pasty resulting in an aesthetically displeasing to the touch wiping article. Much higher weight ratios such as those above 4:1 will not feel dry and will lather poorly.

Diols according to the present invention have from 5 to 12 carbon atoms. They preferably are alkyl diols such as hexylene glycol, octylene glycol, decylene diol and dodecylene diol as well as combinations thereof. Most preferred is hexylene glycol. Amounts of the diol may range from about 2% to about 40%, preferably from about 10% to about 20%, optimally from about 12% to about 16% by weight of the impregnated composition.

A second essential element of compositions according to the present invention is that of a lathering surfactant. By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair, and yet meet the lathering criteria described above.

The products of the present invention typically comprise a lathering surfactant in an amount from about 0.5% to about 40%, preferably from about 0.75% to about 20%, and more preferably from about 1% to about 10%, based on the weight of the impregnated composition.

A wide variety of lathering surfactants are useful herein and include those selected from the group consisting of anionic, nonionic, cationic, amphoteric and lathering surfactant mixtures thereof.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3\_M+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®.

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3\_M+)CO_2R^2$ where $R^1$ is straight or branched alkyl from about $C_8$– to $C_{18}$, preferably $C_{12}$ to $C_{16}$, an d$R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

(12) Alkyl lactylates wherein the alkyl groups range from 8 to 12 carbon atoms, with sodium lauroyl lactylate sold as Pationic 138 C® available from the Patterson Chemical Company as the most preferred.

(13) Taurates having from 8 to 16 carbon atoms, with cocoyl methyl taurate being preferred.

Nonionic lathering surfactants suitable for the present invention include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di- fatty acid esters of ethylene glycol such as ethylene glycol distearate; fatty add monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are: dimethylododecylamine oxide, oleyldi(2-hydroxyethyl)amine oxide, dimethyloctylamine oxide, dimethyldecylamine oxide, dimethyltetradecylamine oxide, di(2-hydroxyethyl)tetradecylamine oxide, 3-didodecyloxy-2-hydroxypropyldi(3-hydroxypropyl) amine oxide, and dimethylhexadecylamine oxide.

Amphoteric lathering surfactants useful for the present invention include aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Illustrative substances are cocamidopropyl betaine, cocamphoacetate, cocamphodiacetate, cocamphopropionate, cocamphodipropionate, cocamidopropyl hydroxysultaine, cetyl dimethyl betaine, cocamidopropyl PG-dimonium chloride phosphate, coco dimethyl carboxymethyl betaine, cetyl dimethyl betaine and combinations thereof.

A necessary element of the present invention is that of a water insoluble substrate. By "water insoluble" is meant the substrate does not dissolve or readily break apart upon immersion in water. A wide variety of materials can be used as the substrate. The following non-limiting characteristics are desirable: (i) sufficient wet strength for use, (ii) sufficient abrasivity, (iii) sufficient loft and porosity, (iv) sufficient thickness, and (v) appropriate size.

Non-limiting examples of suitable insoluble substrates which meet the above criteria include non-woven substrates, woven substrates, hydro-entangled substrates, air entangled substrates and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, Nylon 610 and the like; polyesters such as Fortrel®, Kodel®, and the polyethylene terephthalate fibers, Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers.

Substrates made from natural materials useful in the present invention can be obtained from a wide variety of commercial sources. Non-limiting examples of suitable commercially available paper layers useful herein include Airtex®, an embossed airlaid cellulosic layer having a base weight of about 71 gsy, available from James River Corporation, Green Bay, Wis.; and Walkisoft®, an embossed airlaid cellulosic having a base weight of about 75 gsy, available from Walkisoft U.S.A., Mount Holly, N.C.

Non-woven substrates made from synthetic material useful in the present invention can also be obtained form a wide variety of commercial sources. Non-limiting examples of suitable non-woven layer materials useful herein include HFE-40-047, an apertured hydroentangled material containing about 50% rayon and 50% polyester, and having a basis weight of about 43 grams per square yard (gsy), available from Vertec, Inc., Walpole, Mass.; HEF 140-102, an apertured hydro-entangled material containing about 50% rayon and 50% polyester, and having a basis weight of about 56 gsy, available from Veratec, Inc., Walpole, Mass.; Novenet® 149-191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex® 149-801, a nubbed, apertured hydro-entangled material, containing about 100% polyester, and having a basis weight of about 70 gsy, available from Veratec, Inc. Walpole, Mass.; Keybak® 951V, a dry formed apertured material, containing about 75% rayon, about 25% acrylic fibers, and having a basis weight of about 43 gsy, available from Chicopee Corporation, New Brunswick, N.J.; Keybak® 1368, an apertured material, containing about 75% rayon, about 5% polyester, and having a basis weight of about 39 gsy, available from Chicopee Corporation, New Brunswick, N.J.; Duralace® 1236, an apertured, hydro-entangled material, containing about 100% rayon, and having a basis weight from about 40 gsy to about 115 gsy, available from Chicopee Corporation, New Brunswick, N.J.; Duralace® 5904, an apertured, hydro-entangled material, containing about 100% polyester, and having a basis weight from about 40 gsy to about 115 gsy, available from Chicopee Corporation, New Brunswick, N.J.; Sontaro® 8868, a hydro-entangled material, containing about 50% cellulose and about 50% polyester, and having a basis weight of about 60 gsy, available from Dupont Chemical Corp.

Most preferred as a substrate for purposes of this invention are non-woven substrates, especially blends of rayon/polyester and ratios of 10:90 to 90:10, preferably ratios of 20:80 to 80:20, optimally 40:60 to 60:40 by weight. A most useful substrate is a 70:30 rayon/polyester non-woven wipe article.

Anywhere from 1 to 100, preferably from 5 to 50 single wipes may be stored within a dispensing pouch or container, preferably a moisture impermeable pouch or container. During storage and between dispensing, the pouch or container is preferably resealable. Single wipe containing pouches may also be employed.

The water insoluble substrates of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the use to further distinguish the surfaces.

The amount of impregnating composition relative to the substrate may range from about 20:1 to 1:20, preferably from 10:1 to about 1:10 and optimally from about 2:1 to about 1:2 by weight.

Impregnating compositions of the present invention may also include silicones of a volatile and non-volatile variety. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the silicones may range from about 0.01 to about 20, preferably from about 0.5 to about 3% by weight of the impregnated composition.

Cationic conditioning agents in monomeric and polymeric type are also useful for purposes of this invention. Examples of the polymeric type include: cationic cellulose derivatives, cationic starches, copolymers of a diallyl quaternary ammonium salt and an acryl amide, quaternized vinylpyrrolidone vinylimidazole polymers polyglycol amine condensates, quaternized collagen polypeptide, polyethylene imine, cationized silicon polymer (e.g. Amodimethicone), cationic silicon polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16 etc. manufactured by the Celanese Company), quaternary ammonium salt polymers (e.g. Mirapol A-15, Mirapol AD-1, Mirapol AZ-1, etc., manufactured by the Miranol Division of the Rhone Poulenc Company). Most preferred is polyquaternium-11 available as Luviquat® PQ 11 sold by the BASF Corporation.

Examples of monomeric cationic conditioning agents are salts of the general structure:

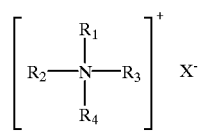

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carbon atoms, or aromatic, aryl or alkaryl groups having from 12 to 22 carbon atoms; and $X^-$ is an anion selected from chloride, bromide, iodide, acetate, phosphate, nitrate, sulfate, methyl sulfate, ethyl sulfate, tosylate, lactylate, citrate, glycolate, and mixtures thereof. Additionally, the alkyl groups can also contain ether linkages, or hydroxy or amino group substituents (e.g. the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicones quats may similarly be employed. Most preferred is Silquat AD designated by the CTFA as Silicone Quaternium 8, available from Siltech Inc.

Amounts of each cationic agent may range from 0.06 to 5%, preferably from 0.1 to 3%, optimally from 0.3 to 2.5% by weight of the impregnated composition.

The disposable, single use personal care cleansing products of the present invention are manufactured by separately or simultaneously adding onto or impregnating into a water insoluble substrate a lathering surfactant and alkyl diol, wherein the resulting product is substantially dry. By "separately" is meant that the surfactants and alkyl diol can be added sequentially, in any order without first being combined together. By "simultaneously" is meant that the surfactants and alkyl diol can be added at the same time, with or without first being combined together.

The surfactant, alkyl diol and any optional ingredients can be added onto or impregnated into the water insoluble substrate by any means known to those skilled in the art. For example, addition can be through spraying, laser printing, splashing, dipping, soaking, or coating.

When water or moisture is used or present in the manufacturing process, the resulting treated substrate is then dried so that it is substantially free of water. The treated substrate can be dried by any means known to those skilled in the art. Non-limiting examples of known drying means include the use of convection ovens, radiant heat sources, microwave ovens, forced air ovens, and heated rollers or cams. Drying also includes air drying without the addition of heat energy, other than that present in the ambient environment. Also, a combination of various drying methods can be used.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

A series of comparative experiments were conducted to evaluate the effect of various alkyl polyols to structure cleansing compositions as impregnates onto substrate wipes of the present invention. Table I lists components and their concentrations for comparative Samples A–G.

TABLE I

| INGREDIENT | SAMPLE (WEIGHT %) | | | | | | |
|---|---|---|---|---|---|---|---|
|  | A | B | C | D | E | F | G |
| Hexylene Glycol | 16.26 | — | — | — | — | — | — |
| Propylene Glycol | — | 16.26 | — | — | — | — | — |
| Butylene Glycol | — | — | 16.26 | — | — | — | — |
| Glycerin | — | — | — | 16.26 | — | — | — |
| Sorbitol | — | — | — | — | 16.26 | — | — |
| Methylpropane Diol (MP Diol) | — | — | — | — | — | 16.26 | — |
| Laureth 4 | — | — | — | — | — | — | 16.26 |
| Polyquaternium 7 (Merquat 2200 ®) | 1.07 | 1.07 | 1.07 | 1.07 | 1.07 | 1.07 | 1.07 |

TABLE I-continued

| INGREDIENT | SAMPLE (WEIGHT %) | | | | | | |
|---|---|---|---|---|---|---|---|
|  | A | B | C | D | E | F | G |
| Cocamidopropyl Betaine (Tegobetaine CKD ®; (82% Active) | 17.60 | 17.60 | 17.60 | 17.60 | 17.60 | 17.60 | 17.60 |
| Decyl Polyglucoside (Plantaren 2000N ®; 50% Active in Water) | 36.09 | 36.09 | 36.09 | 36.09 | 36.09 | 36.09 | 36.09 |
| Sodium Lauroyl Sarcosinate (Hamposyl L-95 ®; 94% Active) | 17.60 | 17.60 | 17.60 | 17.60 | 17.60 | 17.60 | 17.60 |
| Sodium Lauroyl Lactylate (Pationic 138C ®) | 1.65 | 1.65 | 1.65 | 1.65 | 1.65 | 1.65 | 1.65 |
| Capric/Caprylic Triglycerides (Miglyol 812 ®) | 2.50 | 2.50 | 2.50 | 2.50 | 2.50 | 2.50 | 2.50 |
| Silicone Quaternium-8 (Silquat AD ®; 40% Active in Water) | 6.63 | 6.63 | 6.63 | 6.63 | 6.63 | 6.63 | 6.63 |
| Fragrance | 0.40 | 0.40 | 0.40 | 0.40 | 0.40 | 0.40 | 0.40 |
| Glydant Plus ® Liquid (DMDM Hydantoin and Iodopropynyl Butylcarbamate in Butylene Glycol) | 0.20 | 0.20 | 0.20 | 0.20 | 0.20 | 0.20 | 0.20 |

These formulations were prepared in the following manner. Glycol, glycerin, sorbitol or laureth-4, as appropriate, were charged to a mixing vessel. Moderate to vigorous agitation was applied. Thereafter the Merquat 2200® was folded into the batch with mixing until well dispersed. Tegobetaine CKD® was then charged with moderate/vigorous agitation until all clumps of this material disappeared. Decylpolyglucoside was added under continuous agitation. Heat was applied to the batch to achieve 80° C. Then Hamposyl L-95®, Pationic 138C® and Miglyol 812® were sequentially added. Temperatures were lowered to 60° C. allowing addition of Silquat AD®. Upon cooling to 45° C., fragrance and Glydant Plus® Liquid were charged to the batch.

TABLE II

| SAMPLE | RESULTS |
|---|---|
| A | Free flowing liquid |
| B | Thick paste |
| C | Thick paste |
| D | Unable to complete formulation, too viscous after Hamposyl L-95 ® addition |
| E | Unable to complete formulation, too viscous after Tegobetaine CKD ® addition |
| F | Thick paste |
| G | Unable to complete formulation, too viscous after Tegobetaine CKD ® addition |

Evident from Table II was that only the hexylene glycol was able to provide a free flowing liquid which could evenly be distributed onto a substrate cloth. Propylene glycol and butylene glycol resulted in thick pastes which could not easily be utilized in the substrate coating process. Samples D, E and G respectively containing glycerin, sorbitol and laureth-4 could not even be formulated into a spreadable composition. Sample F utilizing methyl propane diol as a structuring aid was too thick for the substrate coating process. It was surprising to find that lower molecular weight glycols such as butylene glycol or propylene glycol were much poorer structuring agents than hexylene glycol. Likewise, higher molecular weight materials such as laureth-4 and sorbitol were poor structuring candidates.

EXAMPLE 2

A set of comparative experiments were conducted similar to those reported under Example 1, except utilizing an alternate surfactant system of sodium cocoylisethionate and cocamidopropyl betaine. The formulations are outlined under Table III.

TABLE III

| INGREDIENTS | SAMPLE (WEIGHT %) | | |
|---|---|---|---|
| | A | B | C |
| Hexylene Glycol | 30.50 | — | — |
| Glycerin | — | 30.50 | — |
| Butylene Glycol | — | — | 30.50 |
| Polyquaternium 7 (Merquat 2200 ®; 95% Active in Water) | 0.80 | 0.80 | 0.80 |
| Sodium Cocoyl Isethionate (Tauranol I-78 ®; 78% Active) | 30.00 | 30.00 | 30.00 |
| Cocamidopropyl Betaine (Tegobetaine CKD ®; 82% Active) | 30.00 | 30.00 | 30.00 |
| Sodium Lauroyl Lactylate (Pationic 138 ®) | 1.70 | 1.70 | 1.70 |
| Silicone Quaternium-8 (Silquat AD ®; 40% Active in Water) | 6.80 | 6.80 | 6.80 |
| Glydant Plus Liquid | 0.20 | 0.20 | 0.20 |

The formulations were prepared by adding either the glycol or glycerin as appropriate, to a reactor vessel. Moderate/vigorous agitation was begun followed by addition of Merquat 2200® and then Tegobetaine CKD®. Heat was applied to achieve 80° C. Tauranol I-78® and then Pationic 138® were sequentially charged to the reactor under agitation. The formulation was then cooled to 60° C. whereupon Silquat AD® was folded into the mixture. Subsequently, the composition was cooled to 45° C. to allow addition of Glydant Plus® Liquid.

TABLE IV

| SAMPLE | RESULTS |
|---|---|
| A | Freely flowing upon batch completion; hardens into solid after 24 hours which can convert at 45° C. into a freely flowing liquid |
| B | Batch could not be completed because formula too viscous |
| C | Batch could not be completed because formula too viscous |

Table IV reports results similar to those found in Example 1. Hexylene glycol was found to be an acceptable structurant. Glycerin and butylene glycol caused unacceptable thickening of the formulations allowing them not to be easily applied to a substrate cloth.

EXAMPLE 3

A set of formulations were prepared to evaluate the effect of weight ratio between hexylene glycol and lathering surfactant. Table V outlines compositions of these formulations.

TABLE V

| INGREDIENTS | SAMPLE (WEIGHT %) | | |
|---|---|---|---|
| | A | B | C |
| Hexylene Glycol | 5.53 | 53.92 | 16.26 |
| Polyquaternium 7 (Merquat 2200) | 1.21 | 0.59 | 1.07 |
| Cocoamidopropyl Betaine (Tegobetaine CKD ®; 82% Active) | 19.86 | 9.68 | 17.60 |
| Decyl Polyglucoside (Plantaren 2000N ®; 50% Active in Water) | 40.72 | 19.86 | 36.09 |
| Sodium Lauroyl Sarcosinate (Hamposyl L-95 ®; 94% Active) | 19.86 | 9.68 | 17.60 |
| Sodium Lauroyl Lactylate (Pationic 138C ®) | 1.86 | 0.91 | 1.65 |
| Capric/Caprylic Triglycerides (Miglyol 812 ®) | 2.82 | 1.38 | 2.50 |
| Silicone Quaternium-8 (Silquat AD ®; 40% Active in Water) | 7.48 | 3.65 | 6.63 |
| Fragrance | 0.45 | 0.22 | 0.40 |
| Glydant Plus ® Liquid (DMDM Hydantoin and Iodopropynyl Butylcarbamate in Butylene glycol) | 0.23 | 0.11 | 0.20 |

TABLE VI

| SAMPLE | WEIGHT RATIO HEXYLENE GLYCOL TO TOTAL SURFACTANT | RESULTS |
|---|---|---|
| A | 1:10 | Unable to finish batch; too viscous after Hamposyl L-95 ® addition |
| B | 2:1 | Wet to the touch; lathers less well than Sample C |
| C | 1:3 | Dry to the touch; excellent latherability |

Samples A–C were prepared in a manner similar to that described for Example 1. These formulations were coated onto a six inch by eight inch rayon/polyester non-woven cloth followed by removal of water in an oven. As reported in Table VI, Sample A was too viscous for the formula even to be completed. In this sample the relative weight ratio of hexylene glycol to surfactant was 1:10. Sample B required a coating of 1.63 grams to achieve 0.44 grams surfactant onto the non-woven cloth. This amount of coating resulted in a wet to the touch feel even after drying in the oven. Lather was also somewhat weaker than from the Sample C towelette. The weight ratio of hexylene glycol to surfactant in Sample B was 2:1.

Sample C required 0.9 grams to place 0.44 grams of surfactant onto the non-woven cloth. The processed cloth had a dry to the touch feel and lather somewhat stronger than the towelette coated with Sample B. The weight ratio of hexylene glycol to total lathering surfactant in Sample C was 1:3.

The foregoing description and examples illustrate selected embodiments of the present invention. In light thereof variations and modifications will be suggested to one skilled in the art, all of which are within the spirit and purview of this invention.

What is claimed is:

1. A substantially dry cleansing product comprising:
   (i) a water insoluble substrate;
   (ii) a lathering surfactant; and
   (iii) a $C_5$–$C_{12}$ alkyl diol, the diol and total lathering surfactant being present in a weight ratio from about 1:1 to about 1:8.

2. The article according to claim 1 wherein the alkyl diol is hexylene glycol.

3. The article according to claim 1 wherein the ratio of alkyl diol to total surfactant ranges from about 1:2 to about 1:6 by weight.

4. The article according to claim 1 wherein the alkyl diol and water have a combined weight relative to total lathering surfactant that ranges from about 3:1 to about 1:5.

5. The article according to claim 1 wherein the lathering surfactant is present in an amount from about 0.5 to about 40% by weight of total impregnated composition deposited upon the water insoluble substrate.

6. The article according to claim 5 wherein the amount of alkyl diol ranges from about 2 to about 40% by weight of the impregnated composition.

7. The article according to claim 1 wherein the water insoluble substrate is a sheet selected from a group consisting of non-woven, woven, hydro-entangled and air entangled substrates.

* * * * *